United States Patent [19]

Mimoun et al.

[11] 4,379,942

[45] Apr. 12, 1983

[54] PROCESS FOR MANUFACTURING METHYL KETONES BY OXIDATION OF TERMINAL OLEFINS

[75] Inventors: Hubert Mimoun, Rueil Malmaison; Robert Charpentier, Villeneuve les Sablons; Michel Roussel, Colombes, all of France

[73] Assignee: Institut Francais du Petrole, Rueil-Malmaison, France

[21] Appl. No.: 265,488

[22] Filed: May 20, 1981

Related U.S. Application Data

[63] Continuation-in-part of Ser. No. 104,941, Dec. 18, 1979, Pat. No. 4,310,704.

[30] Foreign Application Priority Data

Dec. 18, 1978 [FR] France ................. 78 35740
Jan. 11, 1979 [FR] France ................. 79 00828
Nov. 13, 1979 [FR] France ................. 79 28154

[51] Int. Cl.³ .................................. C07C 45/28
[52] U.S. Cl. ............................ 568/385; 568/311
[58] Field of Search .............. 568/385, 342, 311

[56] References Cited

U.S. PATENT DOCUMENTS

| | | | |
|---|---|---|---|
| 3,231,620 | 1/1966 | Cotterill et al. | 568/385 |
| 3,318,891 | 5/1976 | Hausman et al. | 568/400 |
| 3,337,637 | 8/1967 | Norton et al. | 568/311 |
| 3,370,073 | 2/1968 | Clement et al. | 568/338 |
| 3,410,807 | 11/1968 | Lloyd | 252/429 R |
| 3,879,467 | 4/1975 | Zajecek et al. | 568/342 |
| 3,891,711 | 6/1975 | Field et al. | 568/385 |
| 3,927,108 | 12/1975 | van der Moeslyk et al. | 568/342 |
| 3,927,111 | 12/1975 | Robinson | 568/449 |
| 3,932,521 | 1/1976 | Gloyer et al. | 568/401 |
| 4,000,200 | 12/1976 | Cox | 568/311 |

OTHER PUBLICATIONS

Wilkinson et al., J. Chem. Soc., pp. 3632-3637 (1965).

*Primary Examiner*—James H. Reamer
*Attorney, Agent, or Firm*—Millen & White

[57] ABSTRACT

Methyl ketones are prepared in liquid phase by oxidizing terminal olefins of the formula $R-CH=CH_2$, where R is a hydrocarbon radical. The oxidizing agent is hydrogen peroxide or an organic hydroperoxide, and the catalyst is a palladium catalyst of the formula Pd AA' where A is fluoborate, acetate or trifluoroacetate, and A' is $OOR_1$ and where $R_1$ is a hydrocarbon radical.

19 Claims, No Drawings

PROCESS FOR MANUFACTURING METHYL KETONES BY OXIDATION OF TERMINAL OLEFINS

CROSS REFERENCE TO RELATED APPLICATION

The present application is a continuation-in-part of copending application Ser. No. 104,941, filed Dec. 18, 1979 now U.S. Pat. No. 4,310,704.

BACKGROUND OF THE INVENTION

The present invention relates to a process for the selective manufacture of methyl ketones of the formula

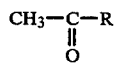

by oxidation, in liquid phase, of olefins of the formula R—CH=CH$_2$. R is alkyl, aryl, aralkyl or alkylaryl hydrocarbon radicals having from 1 to 20 carbon atoms. Non-limitative examples thereof are propylene, 1-butene, 1-pentene, 1-hexene, 1-heptene, 1-octene, 1-decene, 1-dodecene, styrene, and the like.

The method, according to the invention, for manufacturing methyl ketones consists of operating in the presence, on the one hand, of a specific palladium catalyst as defined below and, on the other hand, of an oxidizing agent which is either hydrogen peroxide or a carefully selected organic hydroperoxide.

In the known processes of the Wacker Type, wherein carbonyl compounds are synthesized from olefins, the catalytic system is usually formed of two associated metals, one of them being usually palladium, the other being usually copper or iron, the two metals being used as halides, particularly as chlorides. This catalytic system can be used with water which is the main source of the oxygen incorporated in the ketone.

These processes have however the disadvantage to operate in a very corrosive concentrated hydrochloric acid medium and to necessitate special alloys. Moreover, they are selective only for the oxidation of light olefins such as ethylene and propylene. The production of methylketones from heavier olefins usually results in the formation of undesirable chlorinated materials and aldehydes. Improvements have, however, been brought to the selectivity, when oxidizing heavy olefins, for example, by using organic solvents (French Pat. No. 1,564,635 or U.S. Pat. No. 3,410,807) however the disadvantages associated to the use of the bimetallic system are not avoided.

Other known processes are disclosed in the U.S. Pat. Nos. 3,932,521 and 3,370,073 concerning the oxidation of olefins in the presence of oxygen and a catalyst selected from the group consisting of palladium sulfate, the palladium halides, palladium phosphate and palladium acetate, or a Pd+HCl system. These processes are themselves not sufficiently selective, particularly when using palladium halides or hydrochloric acid.

DETAILED DISCUSSION

One of the advantages of the present process, according to the invention, is to operate in the complete absence of chloride ions, thus avoiding any risk of corrosion. Another advantage is to use a salt or complex of a single metal, palladium.

This process has the main advantage of being selective in the conversion to ketones, of olefins containing up to 20 carbon atoms per molecule, this selectivity being attributable to the choice, as catalyst, of a very specific palladium salt or complex which is used together with an oxidizing agent which is exclusively hydrogen peroxide or a particular organic hydroperoxide. When operating according to the invention, the selectivities are far better than with the use of PdCl$_2$ or Pd+HCl as catalyst system in the presence of hydrogen peroxide, as disclosed in French Pat. No. 1,293,951 (U.S. Pat. No. 3,231,620).

It is to be noted that the U.S. Pat. No. 3,891,711 discloses the use of organic hydroperoxides for converting olefins to ketones in the presence of sulfurized palladium or platinum complexes. However, these complexes have a low activity and they operate at high temperature. They have also a low selectivity.

The catalyst of the invention is a palladium complex of the formula Pd AA' where A is selected from the group consisting of a fluoborate, an acetate or a trifluoroacetate; and A' is OOR$_1$, where R$_1$ is a C$_{3-20}$ hydrocarbon radical preferably selected from the group consisting of tert.-butyl, isopentyl and cumyl. Examples of preferred catalysts to be used in the invention are the following complexes:

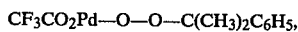

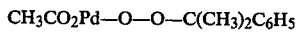

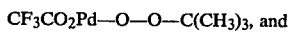

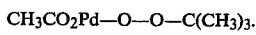

The complexes are preferably produced by reacting an organic hydroperoxide with a palladium compound in accordance with reaction (1) where A and R$_1$ are as defined above:

The compound PdA$_2$ may if desired be prepared in situ, as indicated hereinafter.

An example of reaction 1 is the reaction of t-butyl hydroperoxide with palladium trifluoroacetate, which results in the formation of palladium t-butyl peroxide trifluoroacetate in accordance with reaction 2 (where tBu denotes the t-butyl radical):

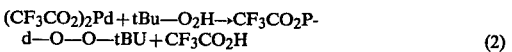

Reaction 1 is generally effected at a moderate temperature of from 0° to 80° C. and preferably from 20° to 40° C. Operation may be effected in the absence or presence of a solvent, for example an aromatic hydrocarbon, an ether or a chlorinated solvent.

In most cases, the peroxide complexes are precipitated from the reaction medium in the form of yellow or orange crystals.

In order to promote substitution of the hydroperoxide radical for the group A, it is often advantageous to operate not only in the presence of the desired hydroperoxide but also in the presence of an alkali metal salt of the hydroperoxide used. Thus for example, adding t-butyl hydroperoxide to a compound PdA$_2$ may be accompanied by the addition of the sodium salt of formula tBu—O—O Na which is produced for example by dissolving metallic sodium in the hydroperoxide.

The palladium carboxylates which can be used in reaction 1 can be prepared in accordance with the method described by G. Wilkinson and his collaborators [J. Chem. Soc. 3632 (1965)] from the metal and carboxlic acid. They can also be produced by reacting the carboxylic acid with a palladium salt such as the nitrate.

The hydroperoxides which can be used for the synthesis of peroxide complexes in accordance with reaction 1 therefore have the general formula $R_1OOH$ in which $R_1$ is a hydrocarbon radical, preferably a tertiary radical, containing from 4 to 20 carbon atoms.

The following may be mentioned as examples of the complexes $ApdOOR_1$ and more particularly those which can be produced in accordance with reaction 1:

palladium t-butyl peroxide acetate (abbreviated to P.P.A.), which has the formula $CH_3CO_2Pd$—O—O—tBu and which is produced directly from palladium acetate and t-butyl hydroperoxide;

palladium t-butyl peroxide trifluoroacetate (abbreviated to P.P.T.), which has the formula $CF_3CO_2Pd$—O—O—tBu and which can be produced from palladium trifluoroacetate and t-butyl hydroperoxide but which can also be prepared from a solution of palladium acetate in trifluoroacetic acid (production in situ of palladium trifluoroacetate) to which an excess of t-butyl hydroperoxide is added.

The following complex can also be produced by the same mode of operation:

$$CF_3CO_2Pd—O—O—C(CH_3)_2C_6H_5$$

from palladium trifluoroacetate and cumyl hydroperoxide.

When the olefins are oxidized with hydrogen peroxide, it is possible to operate without solvent, hydrogen peroxide being however used as an aqueous solution containing, for example, 2 to 98% by weight of peroxide. An aqueous-organic biphasic system may also be used, the aqueous phase consisting of hydrogen peroxide in solution (for example 2 to 98% b.w. of hydrogen peroxide) and the organic phase usually comprising the olefin, the resultant ketone, the palladium catalyst and optionally an organic solvent. This solvent is preferably either a chlorinated solvent (for example chloroform, dichloromethane, dichloroethane, chlorobenzene or another chlorinated hydrocarbon) or an ester (for example ethyl acetate) or an aromatic solvent such as benzene, toluene or xylene, or an alcohol (for example tert-butyl alcohol, tert-amyl alcohol, dimethyl phenyl carbinol and ethylene glycol) or a monocarboxylic acid (for example acetic acid, propionic acid and butyric acid). The use of an organic solvent, and particularly the use of a solvent selected from those specifically listed above results in a substantial improvement of the reaction velocity. Operation in a biphasic system constitutes an advantage when the starting olefin and the resultant ketone are insoluble in the aqueous phase. In that case it is sufficient to decant and separate the two phases. The ketone, which is present in the organic phase, may then be recovered by distillation. The unreacted olefin, the solvent, when used, and the catalyst are then recycled, if desired, into the reaction zone. Finally it is also possible to operate in a monophasic system: a solvent is added to the medium and dissolves both the olefin and the hydrogen peroxide. This solvent is preferably an alcohol (for example methanol, ethanol, ispropanol or tert-butanol) or a cyclic ether (for example tetrahydrofuran or dioxane) or an amine (for example dimethylformamide or hexamethyl phosphoramide).

As a rule, the molar ratio $$\frac{H_2O_2}{\text{olefin}}$$

is advantageously selected from 0.1 to 10 and preferably from B 1.5 to 5.

The ratio $$\frac{\text{olefin}}{\text{catalyst}}$$

by weight is preferably selected from 10 to 10,000 and particularly from 100 to 1,000.

The reaction temperature is usually from 0° to 130° C., particularly from 40° to 70° C.

When the oxidizing agent is an organic hydroperoxide and not hydrogen peroxide, the hydroperoxide is the source of the oxygen atom which is found in the ketone.

The organic hydroperoxide to be used in the present invention has the general formula $R_2OOH$ where $R_2$ is a tertiary alkyl, aralkyl or alkylaryl hydrocarbon group with 4 to 20 carbon atoms.

Non-limitative examples thereof are cumyl hydroperoxide and, most preferably, tert-butyl hydroperoxide. The reaction may be conducted in the absence of a solvent or in the presence of a solvent such as a chlorinated hydrocarbon, for example, dichloroethane, chlorobenzene or dichlorobenzene, an aromatic solvent such as benzene, toluene or xylene or a nitrogen-containing solvent such as nitrobenzene. The olefin/hydroperoxide molar ratio is usually from 0.1 to 10 and particularly from 0.1 to 0.5. The olefin/catalyst molar ratio is usually from 10 to 10,000 and particularly from 100 to 1,000.

The temperature is usually from 0° to 120° C., particularly from 20° to 80° C.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

Synthesis of palladium t-butyl peroxide acetate 1 g (4.5 millimoles) of palladium acetate is dissolved in 8 cc of t-butyl hydroperoxide at ambient temperature (20° C.) with magnetic stirring for a period of 12 hours in a glass reaction vessel. An orange precipitate is gradually formed. This is collected at the end of the reaction, filtered and washed several times with pentane. Evaporation under a high vacuum of the filtrate results in the production of a supplementary amount of the complex. 3.82 millimoles of complex is produced, giving a total yield of 85% of the complex, elementary analysis of the complex corresponding to the formula $CH_3CO_2Pd-O-O-C(CH_3)_3$ (abbreviated to PPA).

The infra-red spectrum of this complex has the characteristic bands of t-butyl (2900–3000 cm$^{-1}$), acetate (1400–1550 cm$^{-1}$) and peroxide (860 cm$^{-1}$) groups.

EXAMPLE 2

Synthesis of palladium t-butyl peroxide trifluoroacetate 1 g (4.5 millimoles) of palladium acetate is dissolved at a temperature of 20° C. in 1 cc of trifluoroacetic acid. 8 cc of t-butyl hydroperoxide is added to the resulting solution. An orange precipitate is then formed. The mixture is stirred for 2 hours at ambient temperature (20° C.) and then the complex is filtered and washed several times with pentane. 4 millimoles is obtained, giving a yield of 88% of a complex in respect of which elementary analysis corresponds to the formula $CF_3CO_2Pd-O-O-C(CH_3)_3$ (abbreviated to PPT). The infra-red spectrum of this complex shows the characteristic bands of trifluoroacetate (1630 and 1200 cm$^{-1}$), t-butyl (3000 cm$^{-1}$) and peroxide (856 cm$^{-1}$) groups.

The same complex can be produced directly from palladium trifluoroacetate and t-butyl hydroperoxide.

EXAMPLE 3

7.15 g of 1-octene, 11 g of 30% by weight aqueous hydrogen peroxide and 74 mg (0.24 mmole) of PPT prepared according to Example 2 are introduced into a heat-insulated glass reactor. The resultant mixture is stirred by means of a magnetic stirrer. After 6 hours, 16.6% of 1-octene is converted. The molar selectivity to 2-octanone is 82%.

EXAMPLE 4

The procedure of Example 3 is repeated, except that 61 mg (0.24 mmole) of PPA prepared according to Example 1 are used instead of the PPT. After 6 hours, 16.5% of 1-octene is converted. The molar selectivity to 2-octanone is 82%.

EXAMPLES 5 TO 8 (COMPARISON)

The operation is the same as in Examples 3 and 4, however with 0.24 millimole of palladium salt or complex which does not conform to the invention.

| EXAMPLE No. | CATALYST | 1-Octene conversion % | MOLAR SELECTIVITY to 2-octanone |
|---|---|---|---|
| 5 | PdCl$_2$ | 17.6 | 56 |
| 6 | PdSO$_4$ | 8.5 | 63.1 |
| 7 | Pd(NO$_3$)$_2$ | 11.5 | 74 |
| 8 | Pd(NO$_3$)$_2$(HMPT)$_2$ | 12.9 | 75 |

EXAMPLE 9

3 cc of 80% tert-butyl hydroperoxide (23 mmoles), 1 cc of 1-octene (6.5 mmoles), 2 cc of toluene, and 25.4 mg of PPA (0.1 mmole) prepared according to Example 1, are introduced into a heat-insulated glass reactor. An argon atmosphere is applied and stirring is performed at a temperature of 50° C. After 4 hours, it is found that 55% of 1-octene is converted and that 2-octanone is formed with a molar selectivity of 76% with respect to the converted 1-octene.

EXAMPLES 10 TO 14 (COMPARISON)

The procedure of Example 9 is repeated, except that 0.1 mmole of a catalyst is used which does not conform to the invention. The results are shown below, including the data of Example 9.

| EXAMPLE No. | CATALYST | 2-OCTANONE formed (millimole) | % MOLAR SELECTIVITY |
|---|---|---|---|
| 9 | CH$_3$CO$_2$Pd—O—O—C(CH$_3$)$_3$ | 3.6 | 76 |
| 10 | Pd(acetylacetonate)$_2$ | 2.1 | 65 |
| 11 | PdCl$_2$(C$_6$H$_5$CN)$_2$ | 0.4 | 30 |
| 12 | Pd[(C$_2$H$_5$)$_2$ NCS$_2$]$_2$ | 0.02 | — |
| 13 | Pd[S$_2$C$_2$(C$_6$H$_5$)$_2$]$_2$ | 0.04 | — |
| 14 | Pd[P(C$_6$H$_5$)$_3$]$_4$ | 2.2 | 60 |

EXAMPLE 15 (COMPARISON)

7.15 g of 1-octene, 18 g of ethyl acetate as organic solvent, 33 g of 30% by weight aqueous hydrogen peroxide and 50 mg (0.28 mmole) of palladium chloride are introduced into a heat-insulated glass reactor. The resultant mixture is stirred magnetically. After 6 hours, 75% of the 1-octene is converted. The molar selectivity to 2-octanone is 56%.

When replacing the 18 g of ethyl acetate with 15 ml of normal hydrochloric acid, it is found, after 6 hours, that 79% of 1-octene have been converted, the molar selectivity to 2-octanone being 47%.

It has also been found that replacement of the hydrogen peroxide oxidizing agent by pure oxygen at a pressure of 1.1 bar under conditions otherwise similar to Example 3 leads to conversion of the 1-octene in 65 minutes, but with a molar selectivity for 2-octanone, of only 38%.

These examples show that the catalysts which do not conform to the invention, and particularly the chlorine and sulfur compounds, have a strongly inhibiting effect on the velocity and selectivity of the reaction.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for producing a methyl ketone of the formula

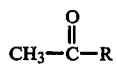

from an olefin of the formula RCH=CH$_2$, wherein R is C$_{1-20}$ hydrocarbyl, said process comprising the step consisting essentially of contacting said olefin in the liquid phase with a palladium catalyst and a peroxide oxidizing agent:

wherein said palladium catalyst has the formula PdAA', wherein A is fluoborate, acetate or trifluoroacetate; and A' is OOR$_1$, wherein R$_1$ is C$_{3-20}$ hydrocarbyl; and wherein said oxidizing agent is hydrogen peroxide or an organic hydroperoxide of the formula R$_2$OOH, wherein R$_2$ is C$_{4-20}$ tertiary alkyl, aralkyl or alkylaryl.

2. A process according to claim 1, wherein the catalyst is a complex having the formula:

CF$_3$CO$_2$Pd—O—O—C(CH$_3$)$_2$C$_6$H$_5$,

CH$_3$CO$_2$Pd—O—O—C(CH$_3$)$_2$C$_6$H$_5$,

CF$_3$CO$_2$Pd—O—O—C(CH$_3$)$_3$, or

CH$_3$CO$_2$Pd—O—O—C(CH$_3$)$_3$.

3. A process according to claim 2, wherein said oxidizing agent is hydrogen peroxide, the molar ratio $$\frac{H_2O_2}{olefin}$$

being from 0.1 to 10, and the ratio by weight $$\frac{olefin}{catalyst}$$

being from 10 to 10,000.

4. A process according to claim 3, wherein the molar ratio $$\frac{H_2O_2}{olefin}$$

is from 1.5 to 5, the ratio by weight $$\frac{olefin}{catalyst}$$

being from 100 to 1,000.

5. A process according to claim 4, wherein hydrogen peroxide is used in aqueous solution.

6. A process according to claim 5, wherein the olefin is further diluted in an organic solvent, said solvent being a chlorinated hydrocarbon, an ester, an aromatic solvent, an alcohol, or a monocarboxylic acid.

7. A process according to claim 6, wherein the solvent is chloroform, ethyl acetate, tert.-butyl alcohol, or acetic acid.

8. A process according to claim 4, wherein the hydrogen peroxide and the olefin are dissolved in an organic solvent, said solvent being an alcohol, a cyclic ether, or an amide.

9. A process according to claim 3, wherein said step is effected at a temperature of 0°–130° C.

10. A process according to claim 4, wherein said step is effected at a temperature of 40°–70° C.

11. A process according to claim 8, wherein said organic solvent is methanol, ethanol, isopropanol, tert.-butanol, tetrahydrofuran, dioxane, dimethylformamide, or hexamethylphosphoramide.

12. A process according to claim 2, wherein said oxidizing agent is tert-butyl or cumyl hydroperoxide, the molar ratio olefin/hydroperoxide being from 0.1 to 10 and the molar ratio olefin/catalyst being from 10 to 10,000.

13. A process according to claim 12, wherein the molar ratio olefin/hydroperoxide is from 0.1 to 0.5, the molar ratio olefin/catalyst being from 100 to 1,000.

14. A process according to claim 12, wherein said step is effected at a temperature of 0°–120° C.

15. A process according to claim 13, wherein said step is effected at a temperature of 20°–80° C.

16. A process according to claim 12, wherein said step is effected in the presence of a solvent, said solvent being a chlorinated hydrocarbon, an aromatic solvent, or a nitrogen-containing solvent.

17. A process according to claim 16, wherein said solvent is dichlorethane, chlorobenzene, dichlorobenzene, benzene, toluene, xylene, or nitrobenzene.

18. A process according to claim 1 wherein in said catalyst, R$_1$ is one of tert.-butyl, isopentyl and cumyl.

19. A process according to claim 1, wherein said step is effected in the absence of chloride ions.

* * * * *